(12) United States Patent
Sauvant et al.

(10) Patent No.: US 6,543,931 B2
(45) Date of Patent: Apr. 8, 2003

(54) METHOD OF EVALUATING THE GLASS-TRANSITION TEMPERATURE OF A POLYMER PART DURING USE

(75) Inventors: Valérie Sauvant, Lyons (FR); Sébastien Duval, Evron (FR)

(73) Assignee: Institut Francais du Petrole, Rueil-Malmaison cedex (FR)

(*) Notice: Subject to any disclaimer, the term of this patent is extended or adjusted under 35 U.S.C. 154(b) by 0 days.

(21) Appl. No.: 09/982,167

(22) Filed: Oct. 19, 2001

(65) Prior Publication Data

US 2002/0048306 A1 Apr. 25, 2002

(30) Foreign Application Priority Data

Oct. 20, 2000 (FR) .............................. 00 13653

(51) Int. Cl.$^7$ .......................... G01N 25/02; G01N 27/22
(52) U.S. Cl. ............................ 374/21; 374/16; 374/35; 324/663
(58) Field of Search ..................... 374/21, 16, 31, 374/35; 324/658, 663, 686–687, 689, 643, 636–639

(56) References Cited

U.S. PATENT DOCUMENTS

| | | | | |
|---|---|---|---|---|
| 4,510,437 A | * | 4/1985 | Iskander | 324/61 R |
| 4,710,550 A | | 12/1987 | Kranbuehl | 324/71.7 |
| 4,723,908 A | * | 2/1988 | Kranbuehl | 432/37 |
| 4,965,206 A | * | 10/1990 | Kell | 435/291 |
| 5,223,796 A | * | 6/1993 | Waldman et al. | 324/687 |
| 5,317,252 A | | 5/1994 | Kranbuehl | 324/71.7 |
| 5,514,337 A | * | 5/1996 | Groger et al. | 422/82.08 |
| 6,028,433 A | * | 2/2000 | Cheiky-Zelina et al. | 324/663 |

FOREIGN PATENT DOCUMENTS

| | | | | | |
|---|---|---|---|---|---|
| EP | 0516367 A2 | * | 5/1992 | | G01N/25/20 |
| EP | 516367 | | 12/1992 | | |
| EP | 0733456 A2 | * | 3/1996 | | B29C/35/02 |
| EP | 0733902 A2 | * | 3/1996 | | G01N/33/44 |
| WO | WO96/42014 | * | 6/1996 | | G01N/33/38 |
| WO | 9642014 | | 12/1996 | | |
| WO | 0036410 | | 6/2000 | | |

OTHER PUBLICATIONS

Dielectric Relaxation Of Poly(ester–ether–carbonate) multi-block Terpolymers, Colloid Polym–Sci 1995.

* cited by examiner

*Primary Examiner*—Diego Gutierrez
*Assistant Examiner*—Gail Verbitsky
(74) *Attorney, Agent, or Firm*—Antonelli, Terry, Stout & Kraus, LLP

(57) ABSTRACT

The proposed method allows to determine by dielectrometry the variation of the glass-transition temperature (Tg) of a polymer material used in the presence of fluids (water/organic compound/gas), pure or in admixture. More precisely, the invention is based on the use of dielectric sensors whose geometry is such that they allow to follow, in a sensitive and reproducible way, the frequency and/or temperature dependence of the dielectric permittivity characteristics of a polymer material in the presence of fluids without disturbing permeation/desorption of the solute during transient and unsteady states, these dielectric measurements (real and/or imaginary part) being connected with the plasticized state of the material, which determines the performances thereof during use.

5 Claims, 1 Drawing Sheet

METHOD OF EVALUATING THE GLASS-TRANSITION TEMPERATURE OF A POLYMER PART DURING USE

FIELD OF THE INVENTION

The absorption of molecular species by diffusion in a polymer material leads to a decrease in the glass-transition temperature (Tg) through plasticization, which modifies the properties and the performances of the material. The examples hereafter show why knowledge of the plasticized Tg is a determining factor as regards applications. In the case of epoxy resins, the Tg loses about 20° C. per percent of absorbed water according to Ellis and Karasz (Ellis, T. S., Karasz, F. E., Polymer, 25, 664, 1984). These resins are conventionally used as a protective anti-corrosion coating, but the range of operating temperatures must be adjusted as a function of the plasticized Tg, because the barrier properties decrease greatly when the Tg is reached. In the case of amorphous or semicrystalline thermoplastic polymers, the Tg is marked by a drop in the mechanical properties thereof. In this case also, the plasticized Tg value has to be taken into account for the range of temperatures used.

Furthermore, the diffusion of molecular species outside a polymer material formulated with plasticizing organic compounds can lead to a Tg increase which modifies the properties and the performances of the material. Following such a phenomenon is also essential in order to be able to control it.

Conventional Tg measuring methods using differential enthalpy analysis (DSC), thermomechanical analysis (TMA) or dynamic mechanical analysis (DMA) lead to overestimated plasticized Tg values because of the dynamic temperature sweep, which leads to a partial desorption of the solute during measurement. Besides, modern industrial practices increasingly involve non-destructive evaluation techniques, which ideally allow to follow certain properties of the materials during use.

BACKGROUND OF THE INVENTION

Thus, dielectrometry emerges as an interesting technique for following the evolution of the resistance and capacitance properties of a polymer material in the presence of fluids, in particular in the presence of water (Hasted, J. B., *Aqueous Dielectrics,* Chapman and Hall, London, 1973). However, it is now an established fact (Maffezzoli, A. M., Peterson, L., Seferis, J. C., Kenny, J., Nicolais, L., *Dielectric characterization of water sorption in epoxy resin matrices,* Polym. Eng. Sci. 1993, 33, 2, 75–82) (Duval, S., Camberlin, Y., Glotin, M., Keddam, M., Ropital, F., Takenouti, H., *The influence of thermal transition to the evaluation of water-uptake in surface polymer film by EIS method,* Proceedings of the 198th meeting of the Electrochemical Society, October 2000) that follow-up of the dielectric properties of a polymer material immersed in water is suitable for studying the diffusion conditions of the solute, but that it does not systematically provide a quantitative measurement of the water uptake, therefore an evaluation of the plasticized Tg by means of Couchman and Karasz type mixing laws (Couchman, P. R., Karasz, F. E., Macromolecules, 11, 117, 1978).

The glass transition of a polymer material corresponds to the development of a generalized mobility on a molecular scale. The complex permittivity $\in^*$ of a polymer material, which is the sum of dipolar and ionic components, can be used as an indicator of the state of the material, and more particularly of the glass transition stage (McCrum, N. G., Read, B. E., Williams, G., *Anelastic and dielectric effects in polymeric solids,* Wiley, J. & Sons, New York 1967). In fact, the development of cooperative dipolar relaxations associated with glass transition (change to high temperatures or low frequencies, because of the kinetic character of the glass transition that follows time/temperature equivalence laws) induces:

an increase in the dipolar component of the real part of the complex permittivity, $\in'_d$;

a dissipative peak on the dipolar component of the imaginary part of the complex permittivity, $\in''_d$.

In cases where ions are present in the medium (for example in form of impurities in the case of thermosetting resins), the glass transition Tg leads to an increase in the ionic conductivity as a result of the mobility development of the chains, hence:

an increase in the ionic component of the real part of the complex permittivity, $\in'_i$, if the accumulation of ions at the electrodes causes a polarization phenomenon;

an increase in the ionic component of the imaginary part of the complex permittivity, $\in''_i$.

U.S. Pat. No. 5,317,252 by Kranbuehl describes in particular how to follow the life of a plastic material exposed to an aggressive environment by means of the dielectric permittivity characteristics of a sensor. Among other properties, he claims the follow-up of the Tg by correlating the permittivity measurements of the material in the initial state with those of the material during use. In fact, temperature and/or frequency dynamic dielectric measurements allow to detect the glass transition (McCrum, N. G., Read, B. E., Williams, G., *Anelastic and dielectric effects in polymeric solids,* Wiley, J. & Sons, New York 1967) which is reflected in the development of cooperative dipolar relaxations in the medium. However, so far, no method allowing quantitative determination of the Tg of a polymer material exposed to an aggressive environment has been proposed.

Furthermore, in the case of measurement of the Tg of a polymer material in the presence of fluids, using the electrodes claimed in patent U.S. Pat. No. 5,317,252 provides no satisfactory answer:

(i) In the case of interdigitated comb sensors on an inert support ($Al_2O_3$ substrates or glass as described in patents U.S. Pat. No. 4,710,550 and U.S. Pat. No. 4,723,908), the impervious character of the substrate leads to an accumulation of the solute at the interface, hence a sensor response saturation before the steady state is established (see Maffezzoli, A. M., Peterson, L. and Seferis) by short-circuit of the two electrodes.

(ii) In the case of interdigitated comb sensors on an organic substance (thermosetting and thermoplastic substrates) deposited at the surface of the polymer material to be studied, the response connected with the polymer material studied cannot be distinguished from that of the polymer substrate.

(iii) In the case of plane/plane sensors to be embedded in the polymer to be studied, the imperviousness of each electrode blocks the free circulation of the solute in the inter-electrode space. The dielectric measurement is therefore not representative of the material in mass in the stationary or transient state.

(iv) Finally, in the case of <<coupon>> sensors exposed to the same environment as the polymer material to be studied, whose complex permittivity changes would be connected by a chart to the evolution of the properties of the polymer material to be studied, the reliability of the sensor is difficult to guarantee, as underlined by D. E. Kranbuehl himself in patent U.S. Pat. No. 5,614,683.

SUMMARY OF THE INVENTION

The aim of the present invention is to provide a method of evaluating the glass-transition temperature of a polymer part during use, and a device suited for implementing this method.

The first object of the invention is a method allowing to evaluate the plasticization/deplasticization of the Tg of a polymer material in the presence of fluids from dynamic measurements of the components of the complex permittivity $\in^*$ of the material ($\in^* = \in' - i\in''$). The method is applicable in the laboratory as well as in an industrial context (in-situ measurements on coatings, sheaths, etc., in particular in the petroleum sphere). At a fixed temperature, the frequency measurements of $\in'$ and $\in''$ are carried out, then adjusted by means of a Havriliak-Negami type parametered equation (Havriliak, S.Jr., Negami, S., J. Polym. Sci. Part C, 1966, No.14, p.99) in order to determine the characteristic time of the glass transition $\tau$ and consequently the plasticized Tg, by considering the previously established relaxation chart of the polymer material in the initial state (before plasticization or deplasticization).

The second object of the invention is a device for measuring the dielectric properties of a polymer material in the presence of fluids (water/organic compound/gas, including any combination), a device suited to transient and steady states.

A first device is designed for laboratory and industrial applications. The pattern of the electrodes, their configuration, and the nature of the conducting material that constitutes the electrodes are controlled so as not to substantially disturb the permeation of the solute, in order to measure the dielectric response of the mass plasticized polymer material. The electrodes according to the invention have a plane/plane capacitor configuration. They are inserted in the polymer material to be studied or deposited at the surface thereof, so that an electric field applied between the electrodes allows to measure the dielectric properties of the material in the air gap by means of an impedance analyzer; one of the two electrodes at least is a comb, a grid or a sintered metal of carefully designed geometry so as not to substantially disturb the permeation of the solute.

A second laboratory device, referred to as <<double-compartment setup>>, allows, by means of an impedance analyzer, to follow the dielectric properties of a polymer film placed between two cells filled with a conducting fluid: salt water/organic compound containing an additive so as to be conducting/gas, including any combination except gases alone. Application of an electric field between two electrodes consisting of an inert conducting material and arranged in a plane-plane configuration at the end of each cell thus allows to characterize the polymer film in the presence of the conducting fluid since the latter acts as an electrolyte and leads the field lines to the polymer film.

The method according to the invention affords the advantage of evaluating the Tg of a polymer material without influencing the measurements because of the technique involved. This method is particularly well-suited for determining the Tg upon plasticization or deplasticization of a polymer material in the presence of fluids. In fact, the proposed method does not require removal of the material from the medium causing plasticization or deplasticization, and it does not modify the absorption or desorption phenomenon. Advantageously, the device for implementing measurement of the Tg of a polymer material does not influence the plasticization or deplasticization phenomenon.

The invention can be defined in general as a method of evaluating the glass-transition temperature of a polymer material during use, wherein the following stages are carried out:

a) determining the glass-transition temperature of the polymer material in the initial state by means of a conventional method, b) bringing two electrodes into contact with a part made of polymer material in the initial state, c) setting up the relaxation chart of said part made of polymer material in the initial state by means of complex permittivity measurements obtained with said electrodes, d) determining a characteristic time of relaxation of the polymer material in the initial state by means of said chart and of the glass-transition temperature determined in stage a), e) setting up the relaxation chart of the same polymer material during use with the same method as in stage b) and c), f) determining the glass-transition temperature of the polymer material during use by means of the relaxation chart set up in stage e) and of the characteristic time determined in stage d).

According to the method of the invention, an alternating electric field can be applied to the polymer part contained in the air gap of the electrodes and the alternating current developed is measured in order to calculate the complex impedance, then the complex permittivity of said polymer part.

According to the method of the invention, the complex permittivity can be measured as a function of the temperature of the polymer part and of the frequency of the electric signal applied at the electrodes.

According to the method of the invention, the relaxation chart can be set up as a function of the temperature by means of the complex permittivity measurements adjusted by a Havriliak-Negami type parametered equation.

According to the method of the invention, the glass-transition temperature can be determined in stage a) by means of a differential enthalpy analysis (DSC).

The invention also relates to a device for determining the glass-transition temperature of a polymer part during use, comprising two electrodes brought into contact with a polymer part, an impedance analyzer which applies an electric signal to the electrodes, a means for recording and displaying the information provided by said impedance analyzer, characterized in that said electrodes are deposited directly and without a support in contact with the material of the polymer part.

Advantageously, at least one of said electrodes has the shape of a comb or of a grid, or it is a part made of sintered metal. Thus, the electrode does not disturb the permeation of the solute in the polymer part.

According to the device of the invention, at least one of said electrodes is a continuous surface. The continuous surface can be a plate made of an electrically conducting material. The device can be applied to a flexible pipe made of polymer reinforced by a metallic armour. In this configuration, the electrode in form of a continuous surface consists of the armour itself.

According to an embodiment of the device, at least one of said electrodes is embedded in the material of the polymer part. According to another embodiment of the device, at least one of said electrodes is deposited on the surface of the material of the polymer part.

According to another embodiment of the invention, the device for determining the glass-transition temperature of a polymer part during use comprises two electrodes brought into contact with a polymer part, an impedance analyzer which applies an electric signal to the electrodes, a means for recording and displaying the information provided by said impedance analyzer, and it is characterized in that said electrodes are brought into contact with the polymer part by means of a conducting fluid.

BRIEF DESCRIPTION OF THE DRAWINGS

Other features and advantages of the invention will be clear from reading the description hereafter, with reference to the accompanying drawings wherein.

DETAILED DESCRIPTION

The polymer materials likely to be characterized by means of the proposed method are thermoplastic polymers and thermosetting polymers, pure or in admixture, and by extension the aforementioned polymers in the presence of various fillers (titanium dioxide, carbonates, silicates, barium sulfates, mica, clays, . . . ), or as composite matrices so that the electrodes are not short-circuited (including for example glass fibers, cellulose fibers, or synthetic fibers). The measurements are carried out in the presence of fluids: water/oil/gas ($CO_2$, $H_2S$, $SO_2$, $CH_4$, . . . ) including any possible combination.

The method of evaluating the glass-transition temperature of a part made of a polymer material is structured on two series of measurements.

First (preferably), the material in the initial state is studied in the laboratory so as to set up the relaxation chart of the glass transition in the reference state (characteristic time or frequency of the glass transition as a function of the inverse of the temperature). Frequency measurements of $\in'$ and $\in''$ are therefore carried out at a fixed temperature over a wide range of temperatures including the Tg of the material measured by DSC (the Tg can also be determined by means of another conventional method such as thermo-mechanical analysis or dynamic mechanical analysis). For each temperature, the experimental curve showing the evolution of the permittivity as a function of the frequency is adjusted by a Havriliak-Negami type parametered equation (Havriliak, S.Jr., Negami, S., J. Polym. Sci. Part C, 1966, No.14, p.99) allowing to determine the characteristic time $\tau$ of the glass transition; in fact, this quantity is a parameter of the H-N equation. Determination of $\tau$ allows to calculate the characteristic frequency $f=1/\tau$ associated with the glass transition. The representation of the evolution of log $\tau$ or of log f as a function of the inverse of the temperature constitutes the relaxation chart of the glass transition specific to each polymer material.

Then, during study of the plasticization/deplasticization of a polymer material in the presence of fluids, a multifrequency measurement of the permittivity is carried out under isothermal conditions, then an adjustment of the curve by means of a H-N equation allows to calculate the characteristic time T associated with the glass transition at the temperature considered. When reproduced at various temperatures, this experiment allows to draw the relaxation chart of the plasticized/deplasticized material.

Considering the two relaxation charts of the materials, in the initial and plasticized/deplasticized state, allows to evaluate the temperature variation of the Tg by plasticization/deplasticization.

The following example of evaluation of the glass-transition temperature of a thermosetting resin in the presence of water illustrates the use of the method.

Figure 1:
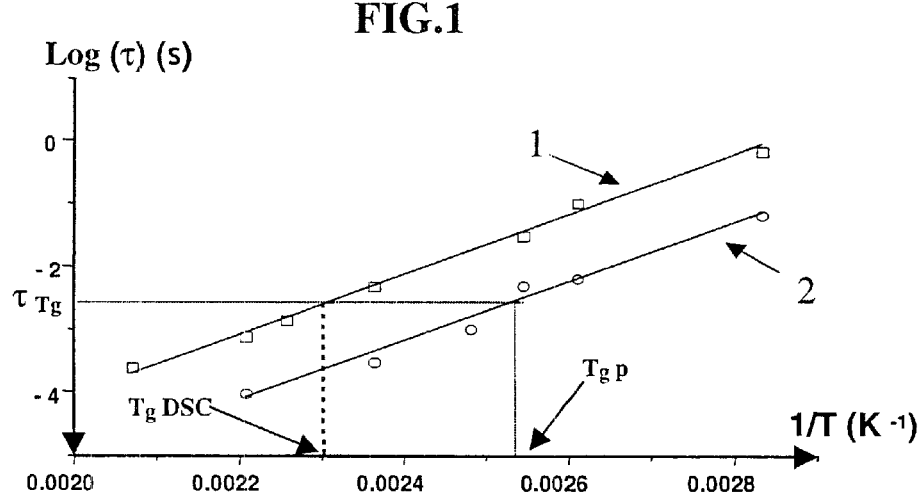
FIG. 1 shows the relaxation chart of the polymer in the initial state and during use.

First, the relaxation chart of the glass transition of the resin in the initial state was set up from multifrequency complex permittivity measurements at different temperatures, ranging between 80° C. and 210° C. At each temperature where the swept frequencies range allows to determine $\in_0$ (permittivity of the relaxed polymer) and $\in_\infty$ (permittivity of the entirely glassy polymer), a Havriliak-Negami type parametered equation is adjusted to the curve so as to determine the characteristic time $\tau$ of the relaxation. This operation allows to draw the relaxation chart log $\tau=f(1/T)$ of the material in the initial state, shown by curve 1 in FIG. 1.

In this example, we define the characteristic time of the glass transition $\tau_{Tg}$ as the time associated in the relaxation chart with the Tg of the polymer material in the initial state Tg DSC, measured as the temperature marking the start of the capacitance jump observed by DSC upon the glass transition stage at a rate of 10° C./minute. In this instance, $\tau_{Tg}$ is $3.10^{-3}$ s and the associated frequency $f_{DSC}$, such that $2\pi f^*\tau=1$, is about 50 Hz.

In the case of the thermosetting resin in the presence of water, measurement of the components of the complex dielectric permittivity is generally carried out under isothermal conditions at a known temperature $T_1$. If the swept frequencies range allows to determine $\in_0$ and $\in_\infty$, a Havriliak-Negami type parametered equation is adjusted to the curve in order to determine the characteristic time $\tau_1$ of relaxation. Assuming that the apparent activation energy of the glass transition is of the same order in the plasticized material as in the non plasticized material, the relaxation chart of the polymer material during use can be drawn (see curve 2 in FIG. 1). The relaxation chart of the polymer in the initial state and during use shown in FIG. 1 being then available, the Tg of the plasticized material Tgp is defined as the temperature associated with the characteristic time $\tau_{Tg}$ on relaxation curve 2 of the material during use.

In this example, the Tg of the resin in the initial state is measured at 160° C. by DSC and the dielectric measurements allow to evaluate the plasticized Tg at about 125° C., a value that is very close to the 120° C. calculated by means of the Couchman-Karasz law, knowing the amount of water absorbed under the gravimetric study conditions. For information, the Tg of the plasticized resin measured by DSC at 10° C./min is clearly overestimated (135° C.).

During the study of plasticization/deplasticization of a polymer material in the presence of fluids, the electrode devices according to the invention are used in such a way that continuous or periodical measurement of the complex permittivity of the polymer material is possible.

The measurements are preferably performed with an impedance analyzer connected to the electrodes on the one hand, and controlled by a computer. The impedance analyzer applies to the polymer material arranged in the air gap of the two electrodes an alternating electric field over a frequency range of 6 decades at the minimum. Measurement of the alternating current developed allows to calculate the complex impedance Z* of the material, which is used as a basis for calculation of complex permittivity $\in^*$ (see U.S. Pat. No. 5,317,252).

The electrodes and the arrangement thereof are designed so as not to substantially disturb the permeation of the solute, in order to measure in the transient and steady state the dielectric response of the mass plasticized polymer material.

Figure 2:
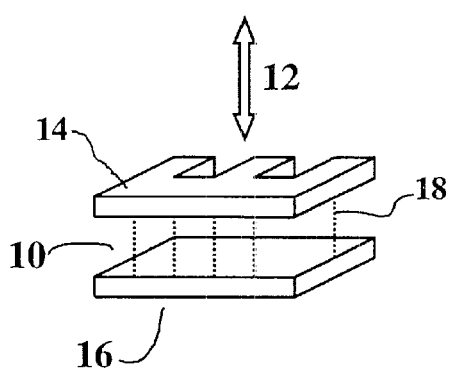
FIG. 2 is a perspective view of the arrangement of a pair of electrodes.

FIG. 2 is a perspective view of the possible arrangement of a pair of electrodes in a plane capacitor configuration, intended for follow-up of the dielectric characteristics of polymer material 10 contained in the air gap. Because of the direction of permeation flow 12 (incoming or outgoing direction), electrode 14 is a comb or a grid deposited on the surface of the polymer material in contact with the fluid or embedded in the polymer mass. Counter-electrode 16, substantially parallel, is preferably plane and rectangular, embedded in the material or an integral part of a polymer-coated metal support. The parallelism between the electrodes is not critical for the invention as long as a magnetic field 18 (field lines in dotted line) can be generated between the two electrodes. Similarly, the shape and the size of electrodes 14 and 16, as well as the potential applied, are not especially important, and their selection notably depends on the response quality of the system for optimizing the measurements. Thus, the approximate applied potential range is included between 10 millivolts to 2 volts, with a commoner range of use between 0.5 volt and 1 volt.

Figure 3:
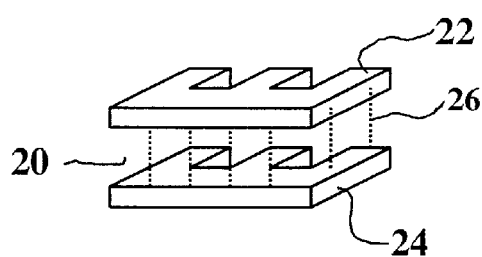
FIG. 3 is a perspective view of a second arrangement of electrodes, FIG. 4 diagrammatically shows a double-compartment setup.

FIG. 3 is a perspective view of another arrangement of electrodes with a plane capacitor configuration, for following the dielectric characteristics of polymer material 20 contained in the air gap. Electrodes 22 and 24 are relatively identical combs or grids, arranged substantially parallel to one another, at least one of the combs being embedded in the material studied. In this case again, the shape and the size of the electrodes, the parallelism between the electrodes and the potential applied are not critical for the invention provided that an electric field 26 (field lines in dotted line) can be generated between the two electrodes and that it allows quality measurement of the properties of the polymer material in the presence of fluids.

According to a variant, electrodes 14, 22 and 24 are sintered noble metal plates allowing to generate an electric field in the air gap without disturbing the permeation of the solute.

In the two devices described above, the thickness of the air gap between the electrodes generally ranges between 0.0025 cm and 2 cm, more commonly between 0.01 cm and 0.5 cm. Precise knowledge of the geometry of the electrode device (in particular the volume of material contained in the air gap and the electrodes-material contact surface common to the electrodes) is not critical for the invention, even if only control of this data allows accurate calculation of the dielectric permittivity values from the complex capacitance C*, easily obtained from the measurement of Z*. In fact, the method used, mentioned in the summary, is based, at fixed T, on an adjustment of the multifrequency dielectric permittivity data by a Havriliak-Negami (N-H) type parametered equation in order to determine the characteristic time of the glass transition $\tau$, hence an evaluation of the plasticized Tg by considering the relaxation chart of the material in the initial state (prior to plasticization or deplasticization), previously set up by means of the same method. The fact that the multifrequency dielectric permittivity values are calculated to within a constant leads to a global quasi-translation of the permittivity curves, but the adjustment by means of the H-N parametered equation remains unchanged.

The electrodes can consist of any inert conducting material, conducting metal, metal alloy or polymer, provided that the durability of the material that constitutes the electrodes does not disturb the measurements. The deposition thickness is not critical for the invention, it generally ranges between 50 nm and 1 mm. The metallic electrodes can be made of platinum or gold for example. The conducting polymers that can be used as electrodes are, for example, doped polytetrafluorethylene, polyvinyl carbazole, ferrocene-based polymers, and silicones or other polymer/organic resin containing electrically conducting additives (graphite fillers for example). In the case where at least one of the two electrodes is deposited on the surface of the polymer material to be studied, good adhesion between the electrode and the substrate is desirable in order to limit parasitic polarization phenomena at the electrodes; adhesion is obtained for example by metallizing the electrode under secondary vacuum, or by depositing a conducting polymer. In the case of an electrode in form of a grid or of a sintered metal part applied onto the surface of the polymer material to be studied, contact is provided by applying a mechanical stress.

Figure 4:
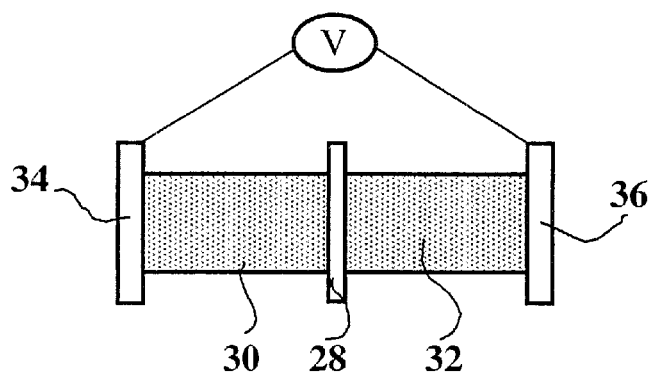

FIG. 4 is a view of the double-compartment setup for following in the laboratory the dielectric characteristics of polymer material 28 inserted between cells 30 and 32 filled with a conducting fluid. Electrodes 34 and 36 are arranged at the end of each cell, substantially parallel. The parallelism between the electrodes, the potential V applied between the electrodes and the conductivity of the fluid are not critical for the invention as long as an electric field can be generated between the two electrodes and that it allows quality measurement of the properties of the polymer material in the presence of fluids.

In the aforementioned setup, the length of the cells generally ranges between 1 cm and 10 cm, more commonly between 3 cm and 8 cm. Precise knowledge of the geometry of the electrode device, in particular the electrodes-electrolyte contact surface, is not critical for the invention, even if only control of this data allows accurate calculation of the dielectric permittivity values from the complex capacitance C*, easily obtained from the measurement of Z*. In fact, as explained above, the method used is based, at fixed T, on an adjustment of the multifrequency dielectric permittivity data: the fact that the multifrequency dielectric permittivity values are calculated to within a constant leads to a global quasi-translation of the permittivity curves, but the adjustment curve remains unchanged.

The electrodes can consist of any inert conducting material, conducting metal, metal alloy or polymer, provided that the durability of the material that constitutes the electrodes does not disturb measurements. The metallic electrodes can be made of glassy carbon or graphite for example. The conducting polymers that can be used as electrodes are, for example, doped polytetrafluorethylene, polyvinyl carbazole, ferrocene-based polymers, and silicones or other polymer/organic resin containing electrically conducting additives (graphite fillers for example).

If the fluid consists of water and/or polar organic solvents such as alcohols, conduction is provided in the fluid by addition of salts (NaCl, LiCl, . . . ) in a proportion generally ranging between 2% and 10% by weight, more precisely between 4% and 6%. If the fluid consists of organic compounds in which the salts are not soluble, the conductivity is provided by adding an inert conducting material in form of a suspended powder, graphite for example.

The method and the device according to the invention notably allow to follow the variation of the Tg of a polymer part during use as a function of the diffusion of molecular species. Knowledge of the Tg during use is a determining factor as regards applications because the stage of glass transition of a polymer material leads to a dramatic drop in certain properties (mechanical performances, barrier properties, . . . ). In the transient state, the evolution of the Tg of a polymer material brought into contact with an aggressive fluid can be followed and the kinetic plasticization parameters can be obtained or, conversely, the deplasticization of a polymer can be studied. Aging of a polymer part can also be followed within the framework of its industrial use. For example, in oil production, the tubes used for carrying oil are made of polymer materials reinforced by a metallic structure. Observation of the evolution of the Tg in situ, on the polymer layers, provides information on the aging thereof.

What is claimed is:

1. A method of evaluating the glass-transition temperature of a polymer material during use, wherein the following stages are carried out:
   a) determining the glass-transition temperature of the polymer material in the initial state by means of a conventional method,
   b) bringing two electrodes into contact with a part made of polymer material in the initial state,
   c) setting up the relaxation chart of said part made of polymer material in the initial state by means of complex permittivity measurements obtained with said electrodes,
   d) determining a characteristic time of relaxation of the polymer material in the initial state by means of said chart and of the glass-transition temperature determined in stage a),
   e) setting up the relaxation chart of the same polymer material during use with the same method as in stage b) and c),
   f) determining the glass-transition temperature of the polymer material during use by means of the relaxation chart set up in stage e) and of the characteristic time determined in stage d).

2. A method as claimed in claim 1, wherein an alternating electric field is applied to the polymer part contained in the air gap of the electrodes and the developed alternating current is measured in order to calculate the complex impedance, then the complex permittivity of said polymer part.

3. A method as claimed in claim 2, wherein the complex permittivity is measured as a function of the temperature of the polymer part and of the frequency of the electric signal applied to the electrodes.

4. A method as claimed in claim 3, wherein the relaxation chart is set up as a function of the temperature by means of complex permittivity measurements adjusted by a Havriliak-Negami type parametered equation.

5. A method as claimed in claim 1 wherein, in stage a), the glass-transition temperature is determined by differential enthalpy analysis (DSC).

* * * * *